US011547419B2

(12) United States Patent
Alzaga et al.

(10) Patent No.: US 11,547,419 B2
(45) Date of Patent: Jan. 10, 2023

(54) SURGICAL STAPLE HAVING TWO MOVABLE BRANCHES CONNECTED BY A TRANSVERSE CONNECTING ZONE

(71) Applicant: INSTITUT HOSPITALO-UNIVERSITAIRE DE CHIRURGIE MINI-INVASIVE GUIDEE PAR L'IMAGE, Strasbourg (FR)

(72) Inventors: Amilcar Alzaga, Mexico City (MX); Peter Halvax, Pecs (HU); Lee L. Swanström, Portland, OR (US); Juan Hernandez, Strasbourg (FR)

( * ) Notice: Subject to any disclaimer, the term of this patent is extended or adjusted under 35 U.S.C. 154(b) by 64 days.

(21) Appl. No.: 16/475,970

(22) PCT Filed: Jan. 3, 2018

(86) PCT No.: PCT/FR2018/050014
§ 371 (c)(1),
(2) Date: Jul. 3, 2019

(87) PCT Pub. No.: WO2018/127659
PCT Pub. Date: Jul. 12, 2018

(65) Prior Publication Data
US 2021/0128154 A1 May 6, 2021

(30) Foreign Application Priority Data
Jan. 3, 2017 (FR) ...................................... 1750041

(51) Int. Cl.
*A61B 17/122* (2006.01)
*A61B 17/128* (2006.01)
*A61B 17/00* (2006.01)

(52) U.S. Cl.
CPC .......... *A61B 17/122* (2013.01); *A61B 17/128* (2013.01); *A61B 2017/00526* (2013.01)

(58) Field of Classification Search
CPC ............ A61B 17/1222; A61B 17/1285; A61B 17/064; A61B 17/0644; A61B 17/068;
(Continued)

(56) References Cited

U.S. PATENT DOCUMENTS 5,470,010 A * 11/1995 Rothfuss ............ A61B 17/0644
227/177.1
2008/0173693 A1* 7/2008 Mas ................... A61B 17/0686
227/175.1

(Continued)

*Primary Examiner* — Brooke Labranche
(74) *Attorney, Agent, or Firm* — Harness Dickey & Pierce, PLC (57) ABSTRACT

The disclosure relates to a surgical staple defining a median folding zone which is continued by a pair of branches, each branch having a pointed fastening end and an intermediate clamping zone situated between the median folding zone and the pointed fastening end. The staple is deformable so that each branch can be folded relative to the median folding zone by causing each fastening end to approach the other branch, the staple being formed by a metal cutout pre-shaped by folding, and is of constant thickness. Intermediate clamping zones of the two branches are cut out such as to form at least two teeth, the edges of which form two complementary clamping surfaces, parallel to the median plane when the staple is folded. The cross-section of clamping surfaces correspond to the cross-section of the metal cutout.

23 Claims, 8 Drawing Sheets

(58) Field of Classification Search
CPC ............... A61B 17/122; A61B 17/128; A61B 2017/00526
See application file for complete search history.

(56) References Cited

U.S. PATENT DOCUMENTS

| | | | |
|---|---|---|---|
| 2008/0269803 A1* | 10/2008 | Safer | ............... A61B 17/0057 606/219 |
| 2009/0093826 A1 | 4/2009 | Warder-Gabaldon | |
| 2009/0272786 A1 | 11/2009 | Zeiner et al. | |
| 2011/0144691 A1 | 6/2011 | Cummins | |
| 2017/0020517 A1 | 1/2017 | Coleman et al. | |
| 2018/0000482 A1 | 1/2018 | Alzaga et al. | |
| 2018/0028181 A1 | 2/2018 | Alzaga et al. | |

\* cited by examiner

SURGICAL STAPLE HAVING TWO MOVABLE BRANCHES CONNECTED BY A TRANSVERSE CONNECTING ZONE

CROSS-REFERENCE TO RELATED APPLICATIONS

This application is a National Phase Entry of International Patent Application No. PCT/FR2018/050014, filed on Jan. 3, 2018, which claims priority to French Patent Application No. 1750041, filed on Jan. 3, 2017, both of which are incorporated by reference herein.

TECHNICAL FIELD

The present invention relates to a staple for internal suturing and ligature as well as the fitting of implants fixed to a tissue by staples during minimally invasive surgery. These staples consisting of a biocompatible metal material (usually made from stainless steel) are used in endoscopic or laparoscopic surgery for holding the two tissue lips in contact or for fixing a prosthesis such as a stent. Such staples have a deformable jaw defined by a separation between the two segments. They must have a space requirement in the deployed position compatible with the passage in the endoscope tube and are manipulated with an applicator placed at the end of the endoscope tube. Unlike staples intended for cutaneous, bone or ocular application, endoscope staples must allow positioning and closure in a very small space with a small possibility of movement.

BACKGROUND

In the prior art various staple solutions intended for endoscopic placing are known. U.S. Patent Publication No. 2011/0144691 provides a staple with a general "U"-shaped with a base extended by two "L"-shaped legs. The legs are folded to form an angle of about 90°. They have a pointed portion perforating the tissues. They also have compression structures placed above the perforation portion limiting the depth of penetration of the perforation portion.

The applicant's international application WO2016128691 describes an earlier version of a surgical staple with two movable branches connected by a transverse connecting zone. Each of these branches has a clamping zone and a fastening end. The transverse connecting zone is deformable to enable said movable branches to be brought approached by folding about the axis of the said transverse connecting zone. This document describes in particular an alternative embodiment of a staple with branches bearing several hooks cut out in the width of the branch and curved, each of the hooks having a clamping surface.

The applicant's international application WO2016128693 describes an endoscopic surgical system formed on the one hand by a plurality of staples and on the other hand by an endoscopic applicator comprising a loader of transversely arranged staples, characterised in that said staples have a central zone and two lateral branches and in that the applicator comprises a movable member having holding means in a transverse plane of a staple to be applied and to ensure the deformation thereof by folding relative to the axis of symmetry of said staple. Other examples of staples known in the prior art are described in the U.S. Patent Publication No. 2009/093826 or in the international patent applications WO2002/19920 or WO2009/135009.

The purpose of the invention is to improve the surgical staples so as to ensure a satisfactory maintenance of the tissues clamped without crushing the tissues if the applied force is too great, nor on the contrary to allow sliding if the force is insufficient or if the tissue moves, and of course by avoiding damaging the lips during the displacement of the clamping zone. The solution provided by the invention relates to the multiplication of the teeth in the clamping zone and a particular configuration of these teeth, as claimed. For endoscope applications, the staple must have a very small size, with structures of a maximum thickness of at least one millimetre and a length of a few millimetres.

Moreover, the staples of the prior art involve a perforation of the tissue lips, thus causing the initiation of a tear. All the staples proposed in the prior art have tips penetrating the tissues deeply in order to ensure holding thereof, which causes lesions of the cell material and sources of infection. Finally, the pressure exerted on the tissues by the staples of the prior art during and after closure is poorly controlled and may cause damage or even local necrosis.

It is therefore very difficult to mass-produce staples having a complex geometry. Moreover, it is difficult to obtain satisfactory holding of the tissues clamped with an elongate tooth, which tends to crush the tissues if the force applied is too great, or on the contrary to allow sliding if the force is insufficient or if the tissue moves. The solution proposed in the "multi-hook" alternative embodiment application WO2016128691 is also not totally satisfactory, because all the forces exerted on the tissue are produced by the single clamping tooth provided on each branch, and because the width of the branches generally does not allow cutting more than one hook, unless the branch is widened, which causes problems of space.

SUMMARY

In order to remedy these disadvantages, the invention, in its broadest sense, relates to a surgical staple according to claim 1, and optionally to one or more dependent claim(s). The invention is different from the earlier art in particular in that each branch has a pointed end, and between this pointed end and the arched connecting zone with the other branch, an intermediate zone provided with a plurality of clamping teeth. The clamping teeth of one branch are arranged symmetrically relative to the clamping teeth of the other branch, so as to come closer by a sweeping movement when the staple is closed, until the edges of the clamping teeth bear on either side of the tissues to be joined, distributing the force over several slices of teeth, unlike in the anterior art. The shape of the teeth is optimized so that the planes formed by the slices of two complementary teeth are substantially parallel in the closed position.

The invention also relates to a system consisting of a surgical staple according to claim 1 and an applicator adapted to be inserted through the operating channel of a flexible endoscope, and comprising a hook adapted to cooperate with the central folding zone, the applicator being provided at its free end with a sleeve having an annular surface capable of forming a stop against which the shoulders formed by the surfaces of the second arched segments are supported, in order to bring the two branches closer together by pivoting about the centre of the arched segment, symmetrically relative to the median plane when pulling in the direction opposite the sleeve. The median plane is defined as the plane passing through the centre of the arched segment joining the two branches and through the centre of the line connecting the two pointed ends. Generally, this median plane is a plane of symmetry of the staple, but according to some alternative embodiments, the pointed ends are not symmetrical relative to this plane. According to a particular alternative embodiment, the inside of the tube is crenellated to allow the transmission of the rotation to the staple by causing the external sheath to start to rotate.

BRIEF DESCRIPTION OF THE DRAWINGS

This invention will be better understood upon reading the following description, with reference to the attached drawings where.

DETAILED DESCRIPTION

Staple

Figures 1, 2:
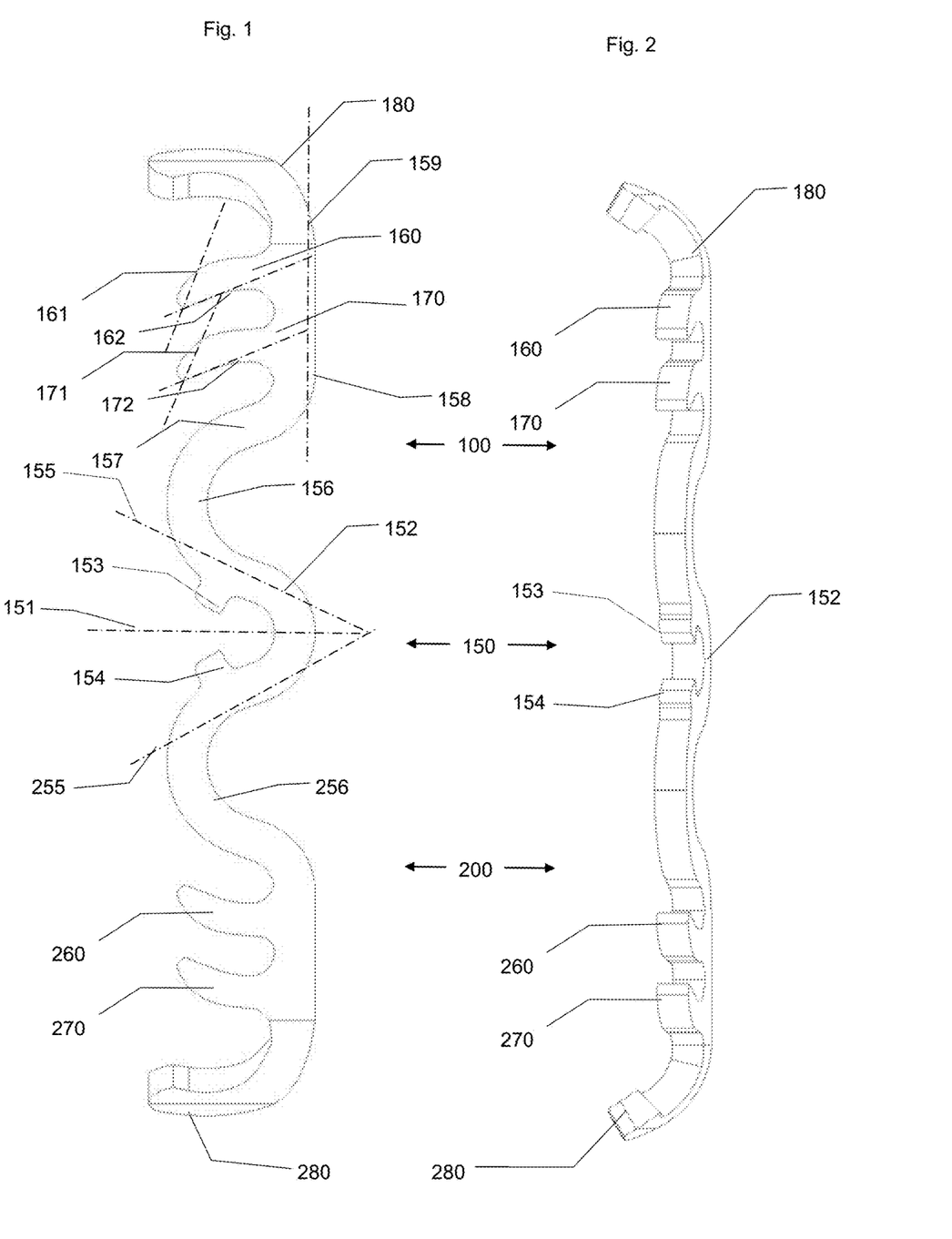
FIGS. 1 and 2 show a respectively front and ¾ face view of a first exemplary embodiment, in the open position.

FIGS. 1 and 2 show a schematic view of a first exemplary embodiment, respectively front and ¾ face view, in the open position. The staple is shown after cutting and folding of the ends, as it is before use. It comprises two branches (100), (200) connected by a median folding zone 150.

The staple is symmetrical relative to a median plane 151 perpendicular to the metal sheet from which the staple is cut, and passing in the middle of the median folding zone (150). The folding zone (150) has a semi-circular-shaped arched segment (152), extending over approximately 90°. This arched segment (152) has at its ends two stops (153, 154) extending perpendicular to the respective tangents (155, 255). These tangents (155, 255) correspond to the tangent of the arched segment 152, at the ends also corresponding to a point where the radius of curvature changes direction. Hereinafter, the description will relate to one of the branches (100), it being understood that the other branch has, symmetrically, the same characteristics.

The arched segment 152 is extended by a second arched segment (156) extending over approximately 90°, with a curvature reversed relative to the curvature of the median arched segment (152). This second arched segment (156) is extended by a third arched segment (157) extending over approximately 45°, with a curvature once again reversed. This third arched segment (157) is extended by a substantially rectilinear segment (158), the longitudinal axis (159) of which is perpendicular to the median symmetry plane (151).

This rectilinear segment (158) has two teeth (160, 170) extending in a direction substantially perpendicular relative to the longitudinal axis 159. These teeth (160, 170) have arched zones (161, 171) directed to the distal side (opposite the median folding zone 152 with a tangent forming an angle of less than 20° relative to a longitudinal axis parallel to the axis (159). On the proximal side, the teeth (160, 170) have arched zones (162, 172), the tangent of which forms an angle between 60° and 120° relative to a longitudinal axis parallel to the axis (159).

Manufacturing Method

The staple according to the invention is produced by cutting from a flat metal sheet, for example by water-jet cutting. The metal sheet has a constant thickness of approximately one millimetre, nominally between 0.8 and 1.5 millimetres. It is produced from a biocompatible material, deformable without elasticity, for example stainless steel or titanium.

From a cutout contained in one plane, the staple may have various curvature profiles. These curvatures may be regular, in a horseshoe for example, or have a profile with variable radii of curvature, for example having sharper curve breaks. These various general curvatures will be advantageous according to the method of use. In the case of use with an applicator suitable for being inserted through the operating channel on a flexible endoscope, the configuration minimising the external envelope of the staple will be favoured. In the case of use with other applicators, it may be advantageous for the staple to conform to the shape of the applicator. After cutting of the staple, the manufacturing method may comprise steps of twisting of certain zones in order to orient them in planes different from the main plane.

Cooperation Between the Staple and the Applicator

Figure 3:
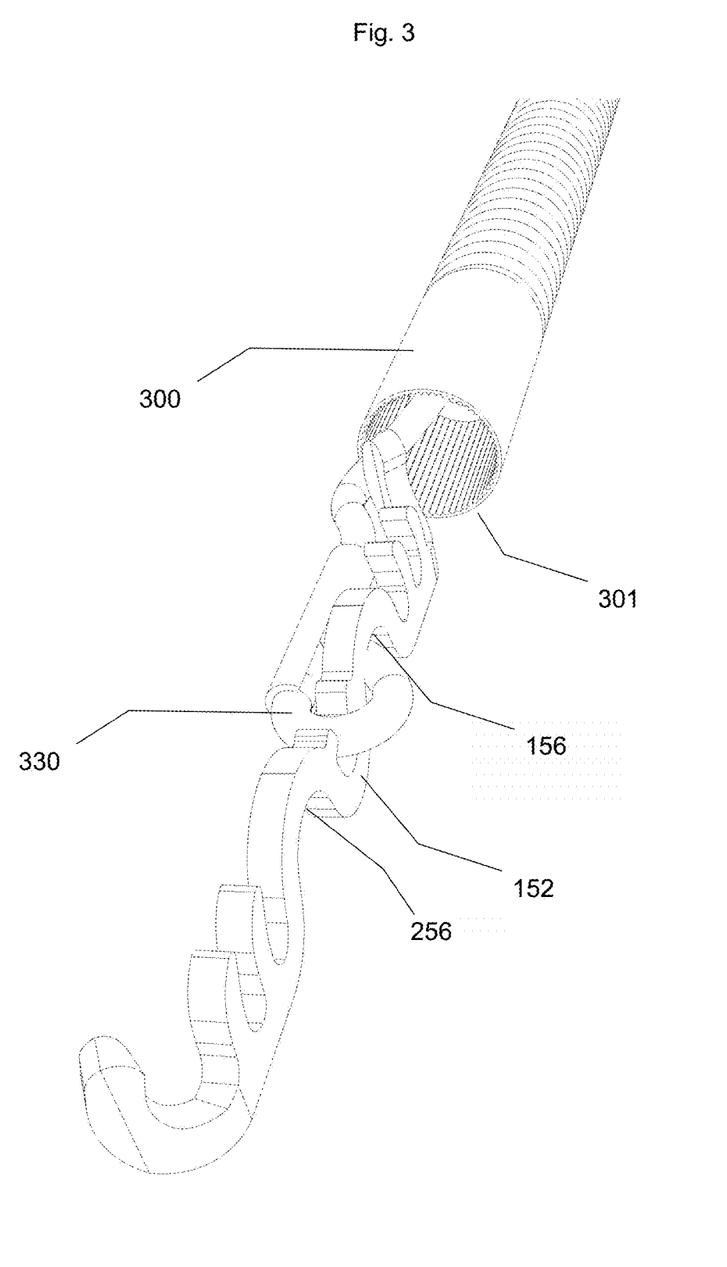
FIG. 3 shows a view of the staple in the partially extended position partially engaged in the applicator before the staple is applied.

The staple can be introduced into a tubular sleeve (300) as shown in FIG. 3. It is introduced into the applicator (300) with the two branches separated at approximately 180°, to make it possible to fit the staple along the longitudinal axis of the applicator. The staple is held by a hook (330) that is engaged in the loop defined by the arched segment (152). This assembly enables the insertion and retraction of the staple in the open position, in the sleeve (300), by means of a longitudinal movement.

When the staple is completely out of the sleeve (300), it can tilt in a perpendicular direction, by pivoting about the hook (330) engaged in the segment (152). The branches are then deployed, still at approximately 180°, but along an axis perpendicular to the axis of the applicator. By next exerting a traction on the hook in the direction of the sleeve (300), the staple comes into contact with the frontal annular surface (301), by means of the surfaces of the arched segments (156, 256). By exerting a longitudinal force, a folding of the staple relative to its median plane (151) is caused. The loop which the staple is mounted on has a complex shape passing round the staple. The inside of the tube may be crenellated to enable the transmission of the rotation of the staple while causing the external sheath to start to rotate.

Figure 4:
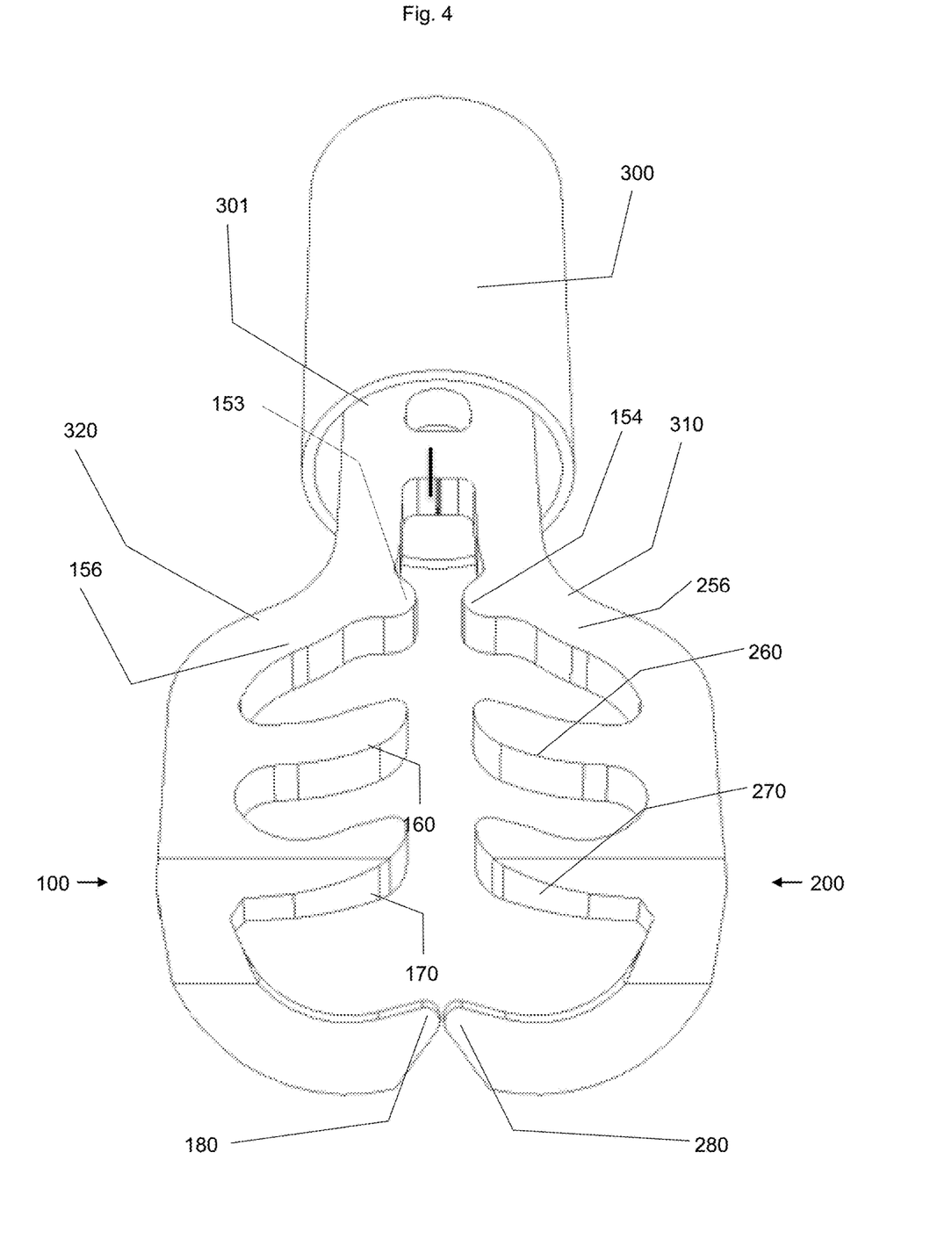
FIG. 4 shows a view of the staple and the applicator after deformation of the staple.

When the staple is folded by a tilting of the branches (100, 200) relative to the centre of the median zone (150), the teeth (160, 170) of one of the branches approaches the teeth of the other branch in order to form clamping zones between the arched zones (161, 171) as shown in FIG. 4. The branch (100) terminates in a hook (180) forming a fastening claw. This hook (180) is twisted relative to the plane of the metal sheet, and has a median plane forming an angle of approximately 30° relative to the median plane 151 of the branches (100, 200). The second branch (200) is symmetrical to the first plane (100) relative to the median plane (151).

When the staple is positioned in the applicator, the relative movement of the sleeve (300) causes the folding of the staple, which then deforms as shown in FIG. 4. The frontal annular surface (301) of the sleeve (300) comes to bear against the shoulders (310, 320) formed by the surfaces of the second arched segments (156, 256), which causes the two branches (100, 200) to come together by pivoting about the centre of the arched segment (152), symmetrically to the mid-plane (151). The radius of curvature of the median segment (152) is slightly less than the internal radius of the sleeve (300).

During this movement of approaching the branches (100, 200) closer together, the two hooks (180, 280) move over an arched path flush with the surface of the tissues to be approached and attaching the two surfaces without perforating them in order to drive them in a movement tending to bring them together and to form two lips that are placed between the teeth (160, 170; 260, 270). These teeth (160, 170; 260, 270) leave a space of 0.5 to 2 millimetres between them, when the two claws (180, 280) come into contact, which ensures holding of the two lips of the tissues to be brought together by clamping, without injuring the tissues. This solution makes it possible to have a staple, the envelope of which in the closed position is larger than the envelope of the applicator, thus making it possible to leave a free space between the lengths of the staple as far as the base of the staple. In the solutions with flexible legs, such as haemostatic staples, the interior space is gradually thinned, the geometry not contributing to the compression but adding to the overall length of the instrument (which is a weakness since this is a nuisance for the practitioner for the remainder of the operation after the application).

Each branch (100, 200) may comprise a plurality of clamping ends, in one of the embodiments favoured for use in flexible endoscopy, each leg comprises two clamping ends. The clamping ends are curved relative to the legs and have a non-traumatic surface, this surface facing the equivalent surface placed on the other leg once the staple is closed. In a use dedicated to compression of the mucous membrane, a free space is described inside the staple.

The presence of a second clamping end makes it possible to increase the compression of the mucous membrane and to improve the holding of the staple after application. As described in the previous paragraph, this end could have other geometries provided that two non-traumatic surfaces face each other once the staple is closed. In the case of use for compression of the mucous membrane, a geometry describing a free space enclosed between the legs of the staple will be favoured. This alternative embodiment is particularly suited to haemostasis and closure on the mucous membrane.

Alternative Embodiment

Figure 5:
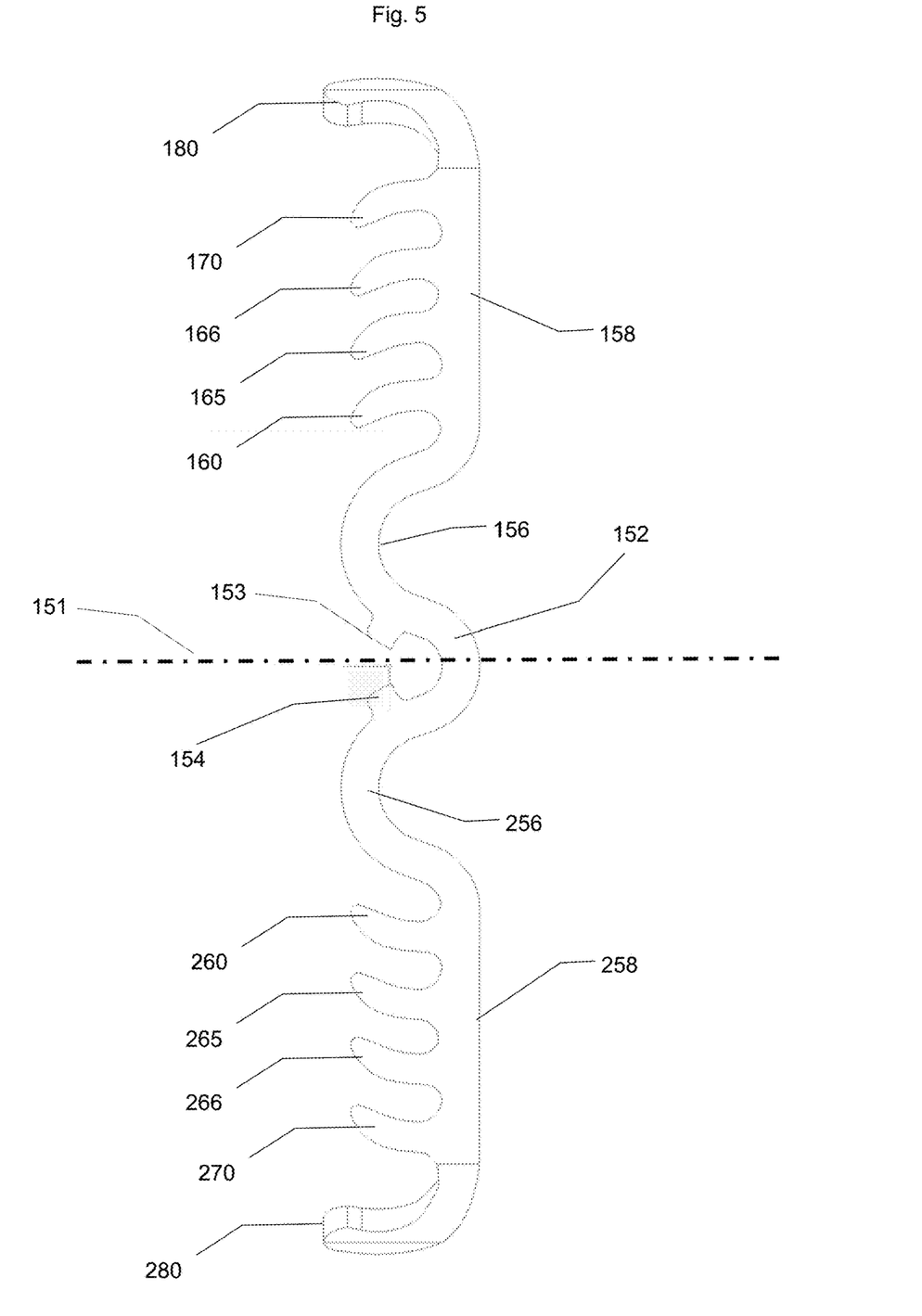
FIG. 5 shows a view of an alternative embodiment.

This alternative embodiment differs from the previous example by the number of teeth. It has an arched median zone (152) with two stops (153, 154) extending perpendicularly. On either side of this arched median zone 152, the staple has arched segments (156, 256) curved in opposite directions. These arched segments (156, 256) are extended by rectilinear segments 158, 258 respectively extending, prior to folding, along an axis perpendicular to the median plane (151). These rectilinear segments (158, 258) are respectively provided with teeth respectively (160, 165, 166, 170; 260, 265, 266, 270). The rectilinear segments respectively (158, 258) are extended by claws respectively (180, 280).

In general terms, the invention is not limited to the examples described by way of non-limitative examples, but with various curvature profiles obtained from a cutout obtained in one plane. These curvatures may be regular, in a horseshoe for example, or have a profile with variable radii of curvature, for example having sharper breaks in curvature. These various general curvatures will be advantageous according to the method of use. In the case of use with an applicator suitable for being inserted through the operating channel on a flexible endoscope, the configuration minimising the external envelope of the staple will be favoured. In the case of use with other applicators, it may be advantageous for the staple to conform to the shape of the applicator.

The clamping and fastening ends may be pointed and bevelled but also non-pointed or rounded. These various configurations correspond to various types of tissue and to various effects. In the case of an application to the mucous membrane, non-pointed bevelled ends will be sufficient to achieve the anchoring, but in the case of the epidermis pointed ends will be necessary.

Figure 6:
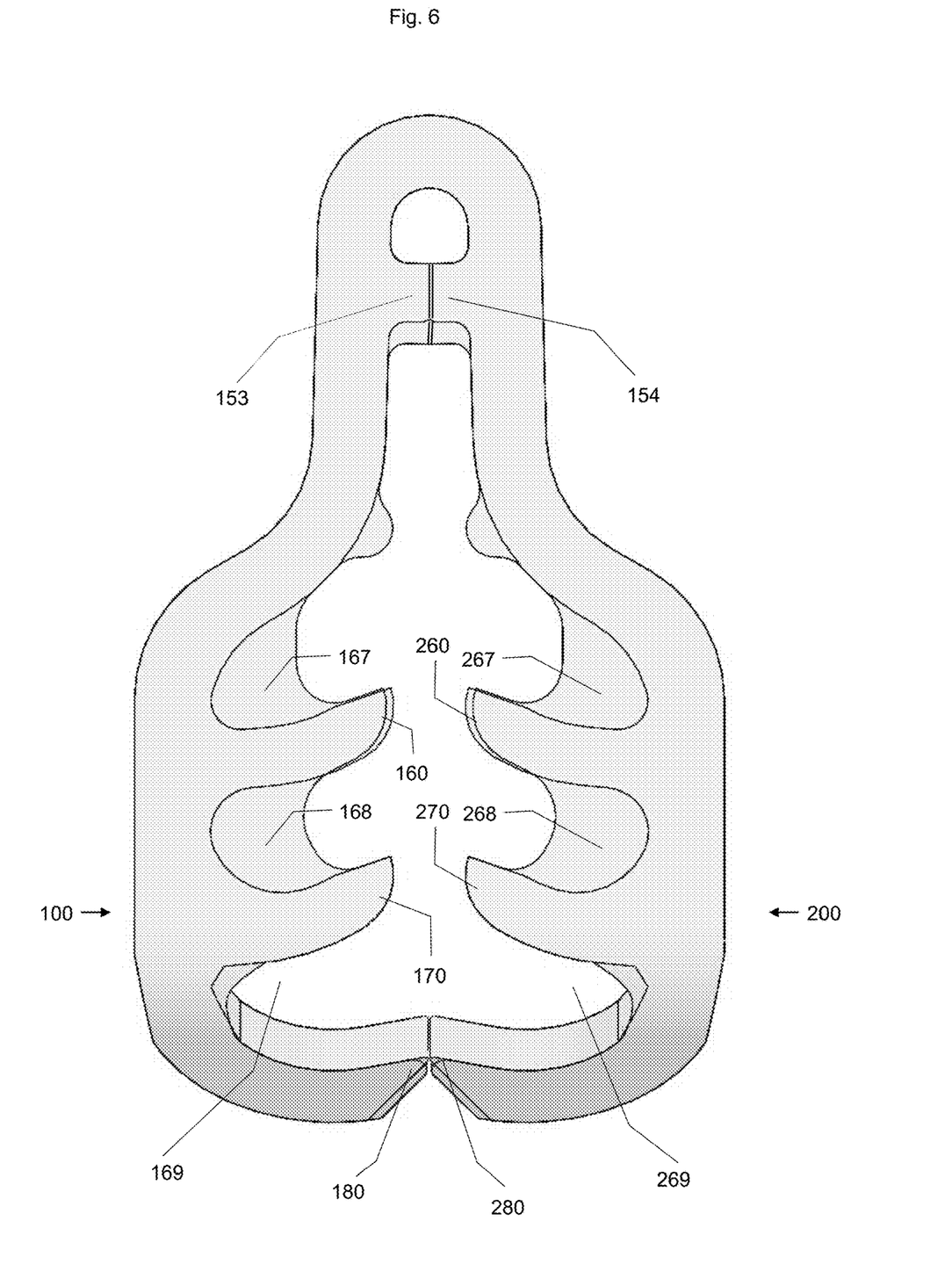
FIG. 6 shows a view of another alternative embodiment.
Figure 7:
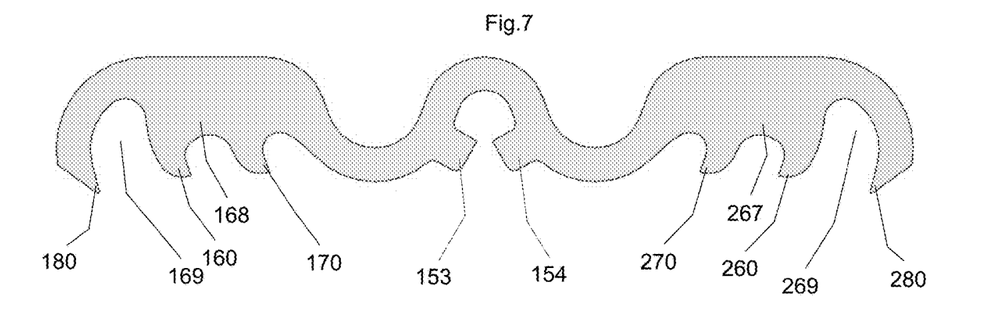
FIGS. 7 and 8 show a view and a detail view of an alternative embodiment.

FIGS. 6 and 7 show front views in the open and closed positions, respectively. The staple corresponding to this alternative embodiment is intended in particular for hemostasis. The inner space (168; 268) between the clamping teeth (160, 170) and 260, 270 respectively is partially "filled" such as to reduce the free space between the branches (100, 200) of the staple after closure and thus improve the compression of the tissues which the staple is positioned on. The space (167, 267) adjacent to the innermost tooth (160, 260) is also partially filled.

Figure 8:
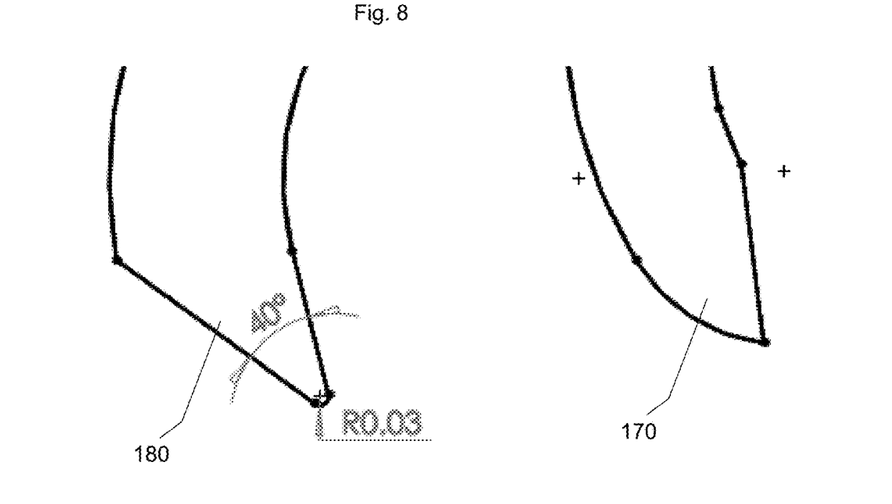

The space (169, 269) adjacent to the outermost tooth (170, 270) is left "hollowed out" to ensure that the staple is firmly anchored in the tissues. The filling can be partial, with a progressive thinning of the thickness of the material filling the space between the two consecutive teeth. FIG. 8 shows an enlarged view of the pointed end (180) of the branch 100 and the outermost clamping tooth 170.

In a preferred version of a staple dedicated to hemostasis, the ends of the teeth (180, 280) are slightly blunt. The external teeth must allow the staple to be anchored to the tissue by reducing the penetration thereof. Advantageously, the staple can be removed by a simple traction, producing minimal superficial tearing of the tissues. In a preferred alternative embodiment illustrated in FIG. 8, the pointed ends (180, 280) have an angle of attack of 40° and a roundness of 0.03 mm.

Figure 9:
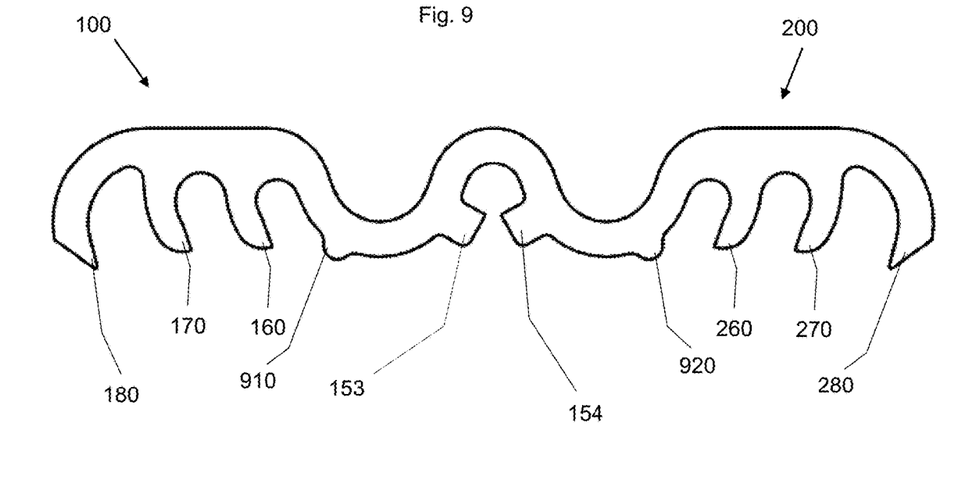
FIG. 9 shows a view of another alternative embodiment.

In the alternative embodiment illustrated in FIG. 9, each of the branches (100, 200) has a small rounded boss (910, 920). Its role is to improve compression and locally stiffen the branch. The torsion of the metal at this point will be reduced by the extra thickness and the deformation will be carried beyond the boss. The placement of this boss and the adjustment of its dimensions allow a more precise control of the geometry of the staple when it is closed.

Figure 10:
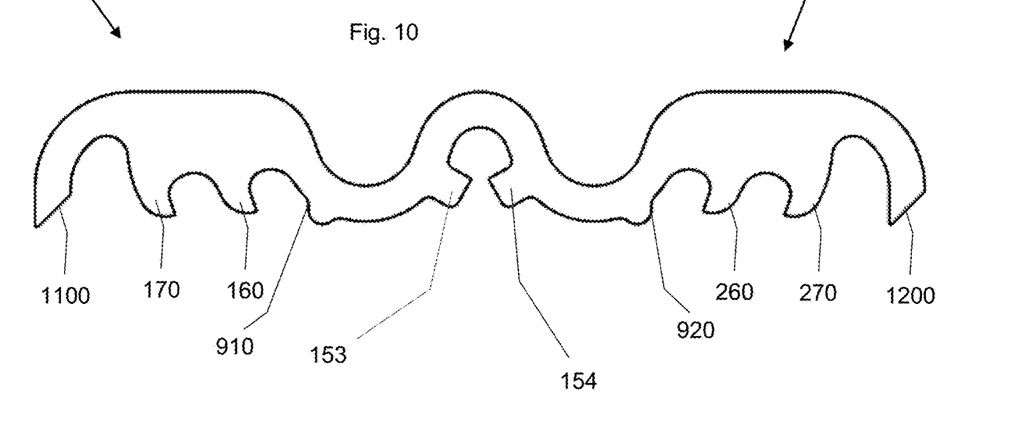
FIGS. 10 to 14 show views of other alternative embodiments.
Figure 11:
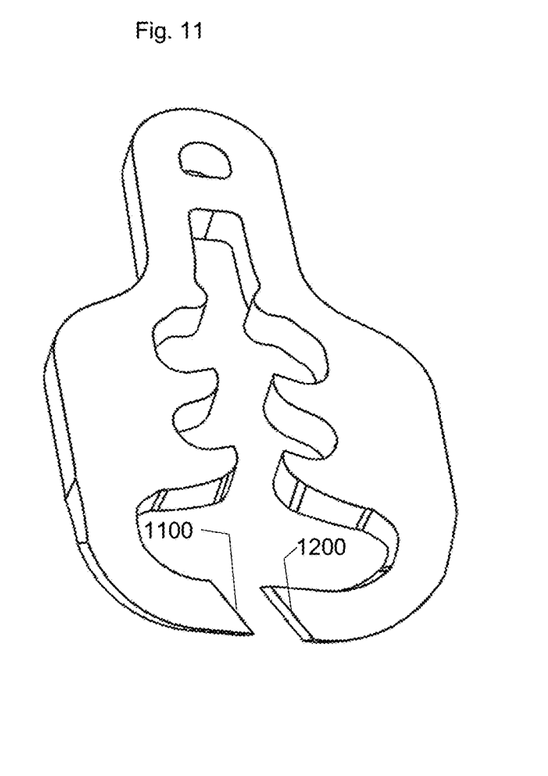
Figure 12:
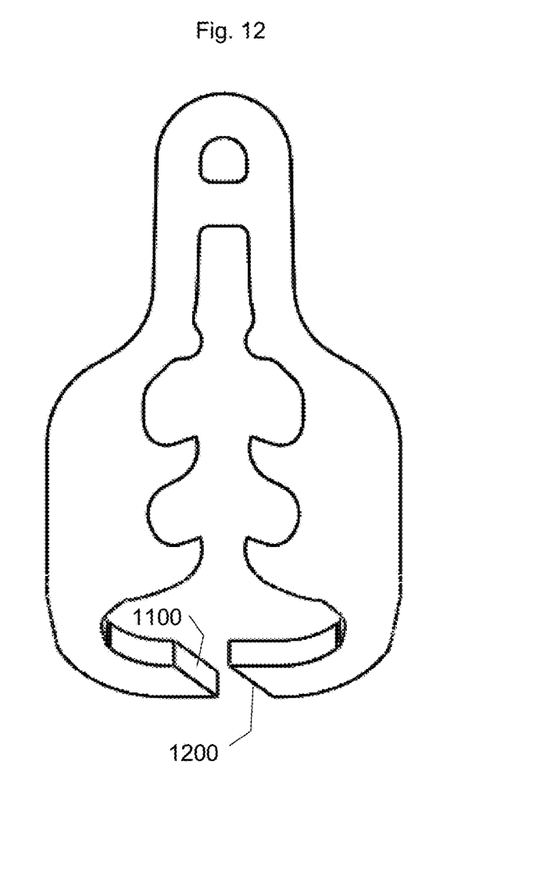
Figure 13:
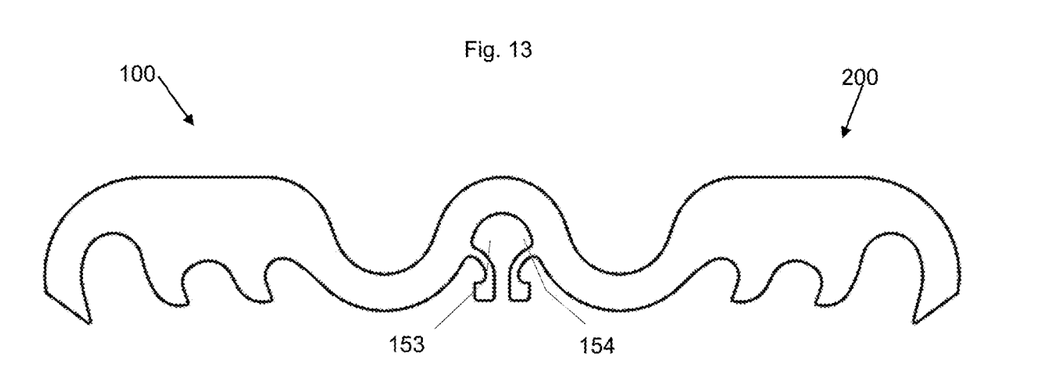
Figure 14:
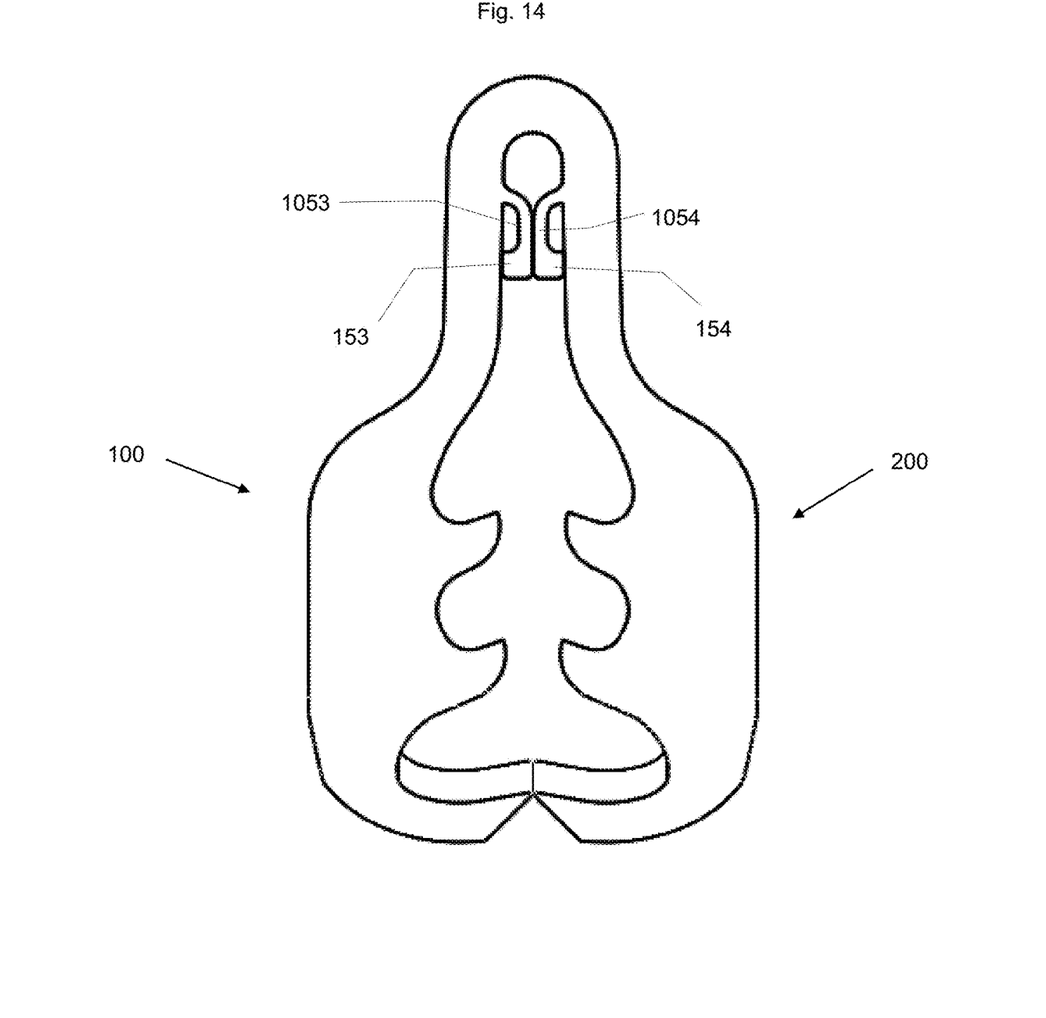

In the alternative embodiment illustrated in FIGS. 10 to 12, the external fastening points (1100, 1200) are not symmetrical. The flank of one is facing outwards and the other inwards. In the alternative embodiment illustrated in FIGS. 13 and 14, the small locking shoulders (153, 154) located on either side of the fastening zone are offset at the end of small deformable legs (1053, 1054). While maintaining the holding function, the space created by the curvature of the legs limits friction with the holding system when the shoulder is released.

Teachings from the Drawings

It is specified that the drawings corresponding to FIGS. 1 to 14 correspond to detailed views of actual alternative embodiments, and not simply schematic views intended only to illustrate in an approximate and schematic manner the principle of the object of the invention. The dimensional characteristics and in particular the dimensional ratios, as well as the radii of curvature, the shapes of the teeth and the different zones of the staple and the relative orientation of the different zones of the staple appearing on the attached drawings are not accidental, but constitute an explicit teaching of certain secondary aspects of the invention. The detailed drawings are intended to provide the skilled person, in the context of the description as a whole, with characteristics that may not be worded verbatim and that technically contribute to a solution to the technical problem posed.

The invention claimed is:

1. A surgical staple comprising a central folding zone which is continued by a pair of branches on a first plane, each branch configured to be perpendicular to a median plane when the staple is in an unfolded position and parallel to the median plane when the staple is in a folded position, the median plane being perpendicular to the first plane, and each branch having an atraumatic end and an intermediate clamping zone situated between the central folding zone and the atraumatic end, the staple being deformable so that each branch can be folded from the unfolded position to the folded position in the first plane relative to the central folding zone by causing each atraumatic end to approach the atraumatic end of the other branch, the staple being formed by a metal cutout, of constant thickness, and the intermediate clamping zone of each of the two branches are cut out such as to form each at least two clamping teeth whose edges form at least two complementary clamping surfaces, the at least two complementary clamping surfaces configured to be perpendicular to the median plane when the staple is in the unfolded position and parallel to the median plane when the staple is in the folded position, and a cross section of each of the at least two clamping surfaces of each of the two branches corresponding to a cross section of the metal cutout, wherein, when in the folded position, the staple is configured to clamp a tissue but not perforate the tissue.

2. A surgical staple according to claim 1, wherein each of the at least two teeth of each of the two branches has a hooked shape.

3. A surgical staple according to claim 1, wherein each of the at least two teeth of each of the two branches has, on a side directed towards the atraumatic end, a convex arched cutout.

4. A surgical staple according to claim 1, wherein each of the at least two teeth of each of the two branches has, on a side directed towards the central folding zone, a concave arched cutout.

5. A surgical staple according to claim 1, being deformed by folding along a pivot axis parallel to a transverse plane.

6. A surgical staple according to claim 1, being deformed by folding along a longitudinal pivot axis and each of the at least two teeth of each of the two branches are folded in a plane perpendicular to a longitudinal plane.

7. A surgical staple according to claim 1, wherein the central folding zone has a semi-circular shape with projecting stops extending perpendicular to each of the branches, to limit the angle of approach of the two branches during folding.

8. A surgical staple according to claim 1, being deformed by folding along a longitudinal pivot axis and the central folding zone has a semi-circular shape with projecting stops extending perpendicular to each of the branches, to limit the angle of approach of the two branches during folding, the stops being folded in a plane perpendicular to a longitudinal plane.

9. A surgical staple according to claim 1, wherein each of the at least two clamping surfaces of each of the two branches are perpendicular to the first plane when the staple is folded.

10. A surgical staple according to claim 1, wherein each of the at least two clamping surfaces of each of the two branches are flat.

11. A system comprising:
(a) a surgical staple comprising a central folding zone which is continued by a pair of branches on a first plane, each branch having a pointed fastening end and an intermediate clamping zone situated between the central folding zone and the pointed fastening end, the staple being deformable so that each branch can be folded in the first plane relative to the central folding zone by causing each pointed fastening end to approach the pointed fastening end of the other branch, the staple being formed by a metal cutout, of constant thickness, and the intermediate clamping zone of each of the two branches are cut out such as to form each at least two clamping teeth whose edges form at least two complementary clamping surfaces, parallel to a median plane when the staple is folded, the median plane being perpendicular to the first plane, and a cross section of each of the at least two clamping surfaces of each of the two branches corresponding to a cross section of the metal cutout, wherein each of the at least two clamping teeth of each of the two branches has a hooked shape; and
(b) an applicator suitable for being inserted through an operating channel of a flexible endoscope, and comprising a hook able to cooperate with the central folding zone, the applicator being provided at its free end with a sleeve having an annular surface able to form a stop against which shoulders formed by surfaces of arched segments come to bear, in order to cause an approach of the two branches by pivoting about a center of the arched segment, symmetrically relative to the median plane when a traction is exerted in a direction opposite the sleeve.

12. A system according to claim 11, wherein each of the at least two teeth of each of the two branches has, on a side directed towards the pointed end, a convex arched cutout.

13. A system according to claim 11, wherein each of the at least two teeth of each of the two branches has, on a side directed towards the central folding zone, a concave arched cutout.

14. A system according to claim 11, wherein the central folding zone has a semi-circular shape with projecting stops extending perpendicular to each of the branches, to limit the angle of approach of the two branches during folding.

15. A system according to claim 11, wherein each of the at least two clamping surfaces of each of the two branches are perpendicular to the first plane when the staple is folded.

16. A system according to claim 11, wherein each of the at least two clamping surfaces of each of the two branches are flat.

17. A system comprising:
(a) a surgical staple comprising:
a central folding zone which is continued by a pair of branches on a first plane, each branch having a pointed fastening end and an intermediate clamping zone situated between the central folding zone and the pointed fastening end,
the staple being deformable so that each branch can be folded in the first plane relative to the central folding zone by causing each pointed fastening end to approach the pointed fastening end of the other branch, and
the staple being formed by a metal cutout, of constant thickness, and the intermediate clamping zone of each of the two branches are cut out such as to form each at least two clamping teeth whose edges form at least two complementary clamping surfaces, parallel to a median plane when the staple is folded, the median plane being perpendicular to the first plane:

(b) an applicator suitable for being inserted through an operating channel of a flexible endoscope, the applicator comprising a hook configured to cooperate with the central folding zone, the applicator being provided at its free end with a sleeve having an annular surface configured to form a stop against which shoulders formed by surfaces of arched segments come to bear, in order to cause an approach of the two branches by pivoting about a center of the arched segment, symmetrically relative to the median plane when a traction is exerted in a direction opposite the sleeve; and (c) an inside of a tube being crenellated in order to enable transmission of rotation of the staple by causing an external sheath to start to rotate.

18. A surgical staple configured to be folded from an unfolded position to a folded position, the staple comprising:

(a) a central segment having a first face in a first plane, a second face in a second plane and parallel to the first face, and a first thickness between the first face and the second face, wherein a median plane bisects the central segment, the median plane perpendicular to the first plane and the second plane;

(b) a first stop extending from the central segment on a first side of the median plane;

(c) a second stop extending from the central segment on a second side of the median plane;

(d) a first branch extending from the central segment, wherein, when in the unfolded position, the first branch is along a longitudinal axis perpendicular to the median plane;

(e) a first hook at a terminal end of the first branch;

(f) a first clamping tooth and a second clamping tooth, each of the first clamping tooth and the second clamping tooth extending from a first side of the first branch and curving toward the central segment, the first clamping tooth and the second clamping tooth located between the first stop and the first hook, the first clamping tooth terminating in a first clamping surface and the second clamping tooth terminating in a second clamping surface;

(g) a second branch extending from the central segment, wherein, when in the unfolded position, the second branch is along the longitudinal axis away from the first branch;

(h) a second hook at a terminal end of the second branch; and (i) a third clamping tooth and a fourth clamping tooth, each of the third clamping tooth and the fourth clamping tooth extending from a first side of the second branch and curving toward the central segment, the third clamping tooth and the fourth clamping tooth located between the second stop and the second hook, the third clamping tooth terminating in a third clamping surface and the fourth clamping tooth terminating in a fourth clamping surface;

(j) wherein the central segment, the first branch, the second branch, the first clamping tooth, the second clamping tooth, the third clamping tooth, and the fourth clamping tooth are within the first plane and the second plane;

(k) wherein the first branch, the second branch, the first clamping tooth, the second clamping tooth, the third clamping tooth, and the fourth clamping tooth each have a thickness equal to the first thickness;

(l) wherein the first branch and the second branch are configured to be folded from the unfolded position to the folded position in the first plane relative to the central segment; and (m) wherein, when in the folded position, the first stop is configured to contact the second stop, the first clamping surface is configured to face the third clamping surface, and the second clamping surface is configured to face the fourth clamping surface.

19. A surgical staple according to claim 18, further comprising:

(a) a first web between the first clamping tooth and the second clamping tooth, a portion of the first web having a thickness less than the first thickness; and (b) a second web between the third clamping tooth and the fourth clamping tooth, a portion of the second web having a thickness less than the first thickness.

20. A surgical staple according to claim 18, wherein each of the first clamping tooth, the second clamping tooth, the third clamping tooth, and the fourth clamping tooth have blunt ends.

21. A surgical staple according to claim 18, further comprising:

(a) a first shoulder extending from the first branch, the first shoulder located between the first stop and the first clamping tooth; and (b) a second shoulder extending from the second branch, the second shoulder located between the second stop and the third clamping tooth.

22. A surgical staple according to claim 18, wherein the first hook and the second hook are at an angle relative to the first plane.

23. A surgical staple according to claim 18, wherein, when in the folded position, the staple is configured to clamp a tissue but not perforate the tissue.

* * * * *